United States Patent [19]

Harris et al.

[11] Patent Number: 5,709,082
[45] Date of Patent: Jan. 20, 1998

[54] MODULATION SCHEMES FOR ON-BOARD DIAGNOSTIC EXHAUST SYSTEM

[75] Inventors: Stephen Joel Harris, Bloomfield Hills; David Kay Lambert, Sterling Heights, both of Mich.

[73] Assignee: General Motors Corporation, Detroit, Mich.

[21] Appl. No.: 654,049

[22] Filed: May 28, 1996

Related U.S. Application Data

[63] Continuation of Ser. No. 266,055, Jun. 27, 1994, abandoned.

[51] Int. Cl.$^6$ ............................................. F01N 3/28
[52] U.S. Cl. ..................... 60/276; 60/277; 73/23.31; 73/118.1; 250/343
[58] Field of Search .................. 60/276, 277; 73/23.32, 73/23.31, 23.2, 117.2, 118.1; 250/338.5, 339.13, 343, 341.2

[56] References Cited

U.S. PATENT DOCUMENTS

| | | | |
|---|---|---|---|
| 3,476,934 | 11/1969 | Luft | 250/344 |
| 3,562,522 | 2/1971 | Cederstrand et al. | 250/252.1 |
| 3,749,495 | 7/1973 | Wilkins et al. | 356/51 |
| 4,013,260 | 3/1977 | McClatchie et al. | 250/343 |
| 4,063,094 | 12/1977 | Schuman | 250/338.1 |
| 4,160,373 | 7/1979 | Fastaia et al. | 73/23.31 |
| 4,336,453 | 6/1982 | Imaki et al. | 250/344 |
| 4,393,304 | 7/1983 | Ishida et al. | 250/343 |
| 4,514,635 | 4/1985 | Ishida et al. | 250/343 |
| 4,560,873 | 12/1985 | McGowan et al. | 250/351 |
| 4,687,934 | 8/1987 | Passaro et al. | 250/343 |
| 4,711,571 | 12/1987 | Schuman | 356/311 |
| 4,902,896 | 2/1990 | Fertig, Sr. et al. | 250/343 |
| 4,922,714 | 5/1990 | Grob et al. | 60/276 |
| 5,060,505 | 10/1991 | Tury et al. | 73/1 G |
| 5,099,680 | 3/1992 | Fournier et al. | 73/23.31 |
| 5,147,426 | 9/1992 | Koike et al. | 73/23.31 |
| 5,239,860 | 8/1993 | Harris et al. | 73/61.48 |
| 5,255,072 | 10/1993 | Mikasa et al. | 356/432 |
| 5,262,645 | 11/1993 | Lambert et al. | 250/339 |
| 5,340,986 | 8/1994 | Wong | 250/343 |
| 5,341,642 | 8/1994 | Kurihara et al. | 60/276 |

*Primary Examiner*—Douglas Hart
*Attorney, Agent, or Firm*—Cary W. Brooks

[57] ABSTRACT

The invention includes an on-board diagnostic system for monitoring exhaust gas from an automotive combustion engine and includes a sample port connected to the exhaust piping, preferably downstream from the catalytic converter. The exhaust port leads to a sample cell to which an infrared spectrometry system is operably connected to measure the concentration of hydrocarbons in the sample cell. An air pump is connected to the exhaust port and communicates with the sample cell. The air pump is operated to continuously purge the sample cell by pushing small amounts of clean air through the sample cell into the exhaust.

3 Claims, 2 Drawing Sheets

MODULATION SCHEMES FOR ON-BOARD DIAGNOSTIC EXHAUST SYSTEM

This is a continuation of application Ser. No. 08/266055 filed on Jun. 27 1994, and now abandoned.

FIELD OF THE INVENTION

This invention relates to modulation schemes for on-board diagnostic exhaust sensors, and more particularly to an automotive exhaust gas diagnostic system using infrared spectrometry and an air pump.

BACKGROUND OF THE INVENTION

Future regulation of the Environmental Protection Agency (EPA) will require all cars and light trucks for the U.S. market to be able to self diagnose malfunction of the catalytic converter used in automobiles to clean automotive combustion engine emissions. An ideal system for this application would be inexpensive, would always detect a failed catalytic converter, and would never give a false reading or alarm. Some systems being proposed for such self diagnosis of catalytic converter malfunction use oxygen sensors exposed to the exhaust stream before and after the catalytic converter to monitor fluctuations in the stream's oxygen concentration at these two locations. The amount by which the fluctuations are damped as the stream passes through the catalytic converter is an indication of the catalytic converter's capability to store oxygen. It is true that new catalytic converters that function properly do exhibit much more oxygen storage than catalytic converters that have been abused to the point that they no longer function. However, the malfunction threshold which is likely to be defined by the EPA is based on the catalytic converter's actual performance in reducing the hydrocarbon concentration in the exhaust. As catalytic converters deteriorate in normal use there is little correlation between their ability to store oxygen and their effectiveness at reducing the hydrocarbon concentration in the exhaust. The false alarm rate of the oxygen storage diagnostic is consequently expected to be high. This will be costly to automobile manufacturers.

Measurement of the concentration of hydrocarbons in automotive combustion engine exhaust has been conducted by service stations using infrared gas analyzers to check for catalytic converter malfunction. These devices typically have an ir source, an ir detector, a sample cell, and a filter wheel that can be rotated to put various ir interference filters in the beam. The ir light from the source passes through an ir filter that only passes light in a band of interest, through the sample where some of the light is absorbed, and to the ir detector which produces an electrical signal. The concentration of a particular gas is monitored by comparing the detected signal between situations with two different filters in the beam: one filter transmits light that is absorbed by the gas of interest, the other filter transmits light at a nearby wavelength that is not absorbed by the gas of interest. The ratio of the detected signals with the two different filters in the beam is a function of the concentration of the gas in the cell. Prior patents that describe such gas analyzers include U.S. Pat. No. 4,013,260 issued Mar. 22, 1977 to McClatchie et al and U.S. Pat. No. 5,060,505 issued Oct. 19, 1991 to Tury et al.

A different type of infrared gas analyzer was used by the EPA until 1972 to verify vehicle compliance with hydrocarbon emission regulations. Gas analyzers of this type detected the ir by monitoring the pressure in a cell that contained the gas of interest. Absorbed ir heated the gas in the cell and caused the pressure to rise. Such a gas analyzer is described in U.S. Pat. No. 3,476,934 issued Nov. 4, 1969 to Luft. Subsequently, the EPA has used a flame ionization detector.

Heretofore there has not been an on-board system to detect hydrocarbons in exhaust gas which is usable as the automobile is in operation on a regular continuous basis. A variety of obstacles stand in the way of such an on-board sensor system. It is well known that automobile combustion engine exhaust includes contamination such as soot, oil and/or dirt. As such substances accumulate on an ir sensor's optics, light transmission through the sensor decreases until it no longer functions. The use of a particulate filter to remove the contamination before it contacts the optical surfaces would overcome this problem but is likely to be unacceptable for an onboard sensor since the filter would eventually become plugged and would have to be replaced. One such particulate filter, used in an off-board gas analyzer where it can be replaced, is described in U.S. Pat. No. 5,049,170 issued Sep. 17, 1991 to Gobel.

A second obstacle is the size and cost of the mechanical assembly used to rotate filters into the ir beam in conventional gas analyzers. One approach to overcome this problem is to use a single ir source and a dual element ir detector, each detector with its own ir filter, as described in U.S. Pat. No. 5,239,860 issued Aug. 31, 1993 to Harris et al and in U.S. Pat. No. 5,262,645 issued Nov. 16, 1993 to Lambert et al. As shown in FIG. 2, the ir that reaches one detector is filtered so that it only interacts with the molecule of interest. The ir that reaches the other detector is filtered so that it is in a nearby band that does not interact with the molecule of interest. The signals from the two detectors are ratioed. The ratio is sensitive to the concentration of the molecule of interest, but it is insensitive to changes that affect the light arriving at both detectors. For example, in one scheme a beam of infrared light is passed through exhaust gas in a sample cell and a dual element detector monitors the transmitted intensity in two wavelength bands. One band, at about 3.4 micron wavelength, is absorbed by hydrocarbons in the exhaust. The other band, at a nearby wavelength where there is much less absorbance of ir by hydrocarbons, is used as a reference. The ratio of the two signals is an indication of the hydrocarbon concentration in the cell.

However, the use of a dual element introduces its own problems. A dual element detector, while commercially available is more costly than a single element detector. Also, at the present time, the filters must be individually cut to fit over the detectors, and they must be carefully glued on so that each detector is sensitive to only the desired wavelength band. Another drawback of the two detector scheme is that the ratio that is calculated from their outputs is sensitive to the relative illumination of the two detectors. If the relative illumination changes as a result of shock or strong vibration, the gas analyzer would need to be recalibrated. One could try to mount the system in such a way as to dampen vibrations, but this solution is expensive and is not certain to work forever.

The present invention overcomes numerous disadvantages of the prior art systems.

SUMMARY OF THE INVENTION

The invention includes an on-board diagnostic system for monitoring exhaust gas from an automotive combustion engine and includes a sample port connected to the exhaust piping, preferably downstream from the catalytic converter. The exhaust port leads to a sample cell to which an infrared spectrometry system is operably connected to measure the concentration of hydrocarbons in the sample cell. An air pump is connected to the exhaust port and communicates with the sample cell. The air pump is operated to continuously purge the sample cell by pushing small amounts of clean air through the sample cell into the exhaust. When a measurement is to be made of the exhaust gas, a valve positioned between the pump and the sample cell is closed so that exhaust gas flows through the sample cell. During the measurement, the valve cycles such that the environment in the cell alternates between exhaust and clean air on a time scale of a few seconds. In the absence of the air pump, exhaust gasses could pass into or through the sample cell, gradually contaminating the optics of the infrared detector system. Further, by alternatively filling the sample cell with exhaust and then with air, the requirements of two wavelengths for the infrared system to be examined is removed. This is because measuring the transmitted intensity when the sample cell is purged is equivalent to measurement at the "reference" wavelength. The result is that a simpler, less expensive one-element detector can be used. Because a single-element detector is used, the alignment requirement disappears. Any long term changes in alignment change the signal, but the ratio of the signals during the reference and the hydrocarbon portion of the cycle is unaffected.

These and other advantages will become apparent from the following brief description of the drawings, detailed description, and appended claims and drawings.

DETAILED DESCRIPTION

Figure 1:
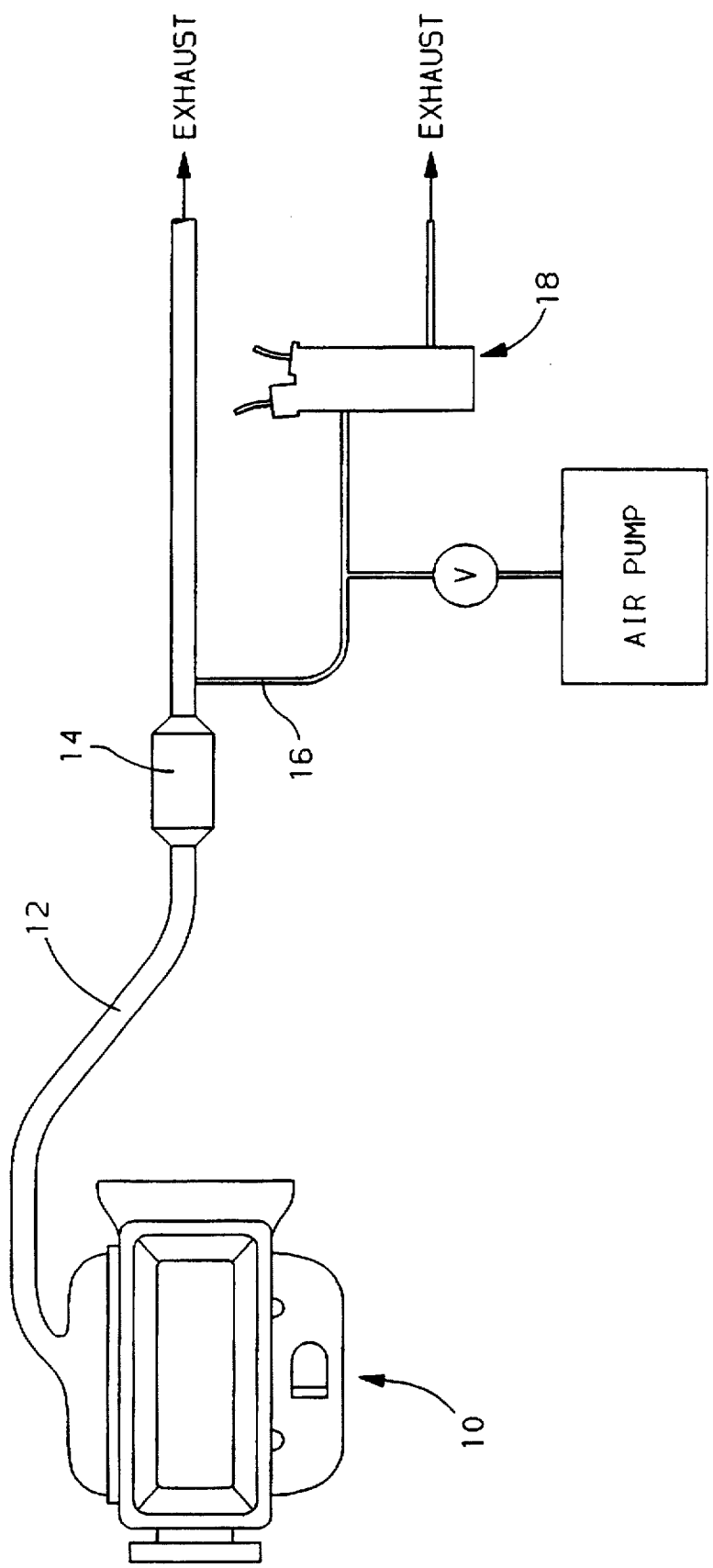
FIG. 1 illustrates an on-board diagnostic system for measuring automotive combustion engine exhaust and for determining the malfunction of catalytic converters.
Figure 2:
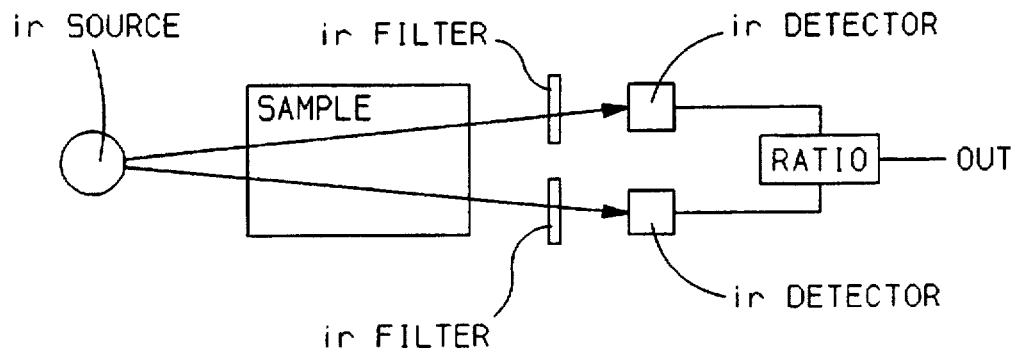
FIG. 2 illustrates an infrared detector system with two detectors.

FIG. 1 shows a system for an on-board diagnostic of automobile combustion exhaust and catalytic converters. The system includes an automobile combustion engine 10 including exhaust piping 12 leaving from the engine to a downstream catalytic converter 14. A sample port 16 is connected to the exhaust piping downstream from the catalytic converter. A sample cell 18 is connected to the exhaust port for sampling small amounts of exhaust gas. An air pump is provided and communicates with the exhaust port. A control valve is positioned between the air pump and the exhaust port. Appropriate electronic circuitry is provided to selectively open and close the control valve so that when the control valve is closed, small amounts of exhaust gas pass into the sample cell for measurement by the infrared detector system.

Figure 3:
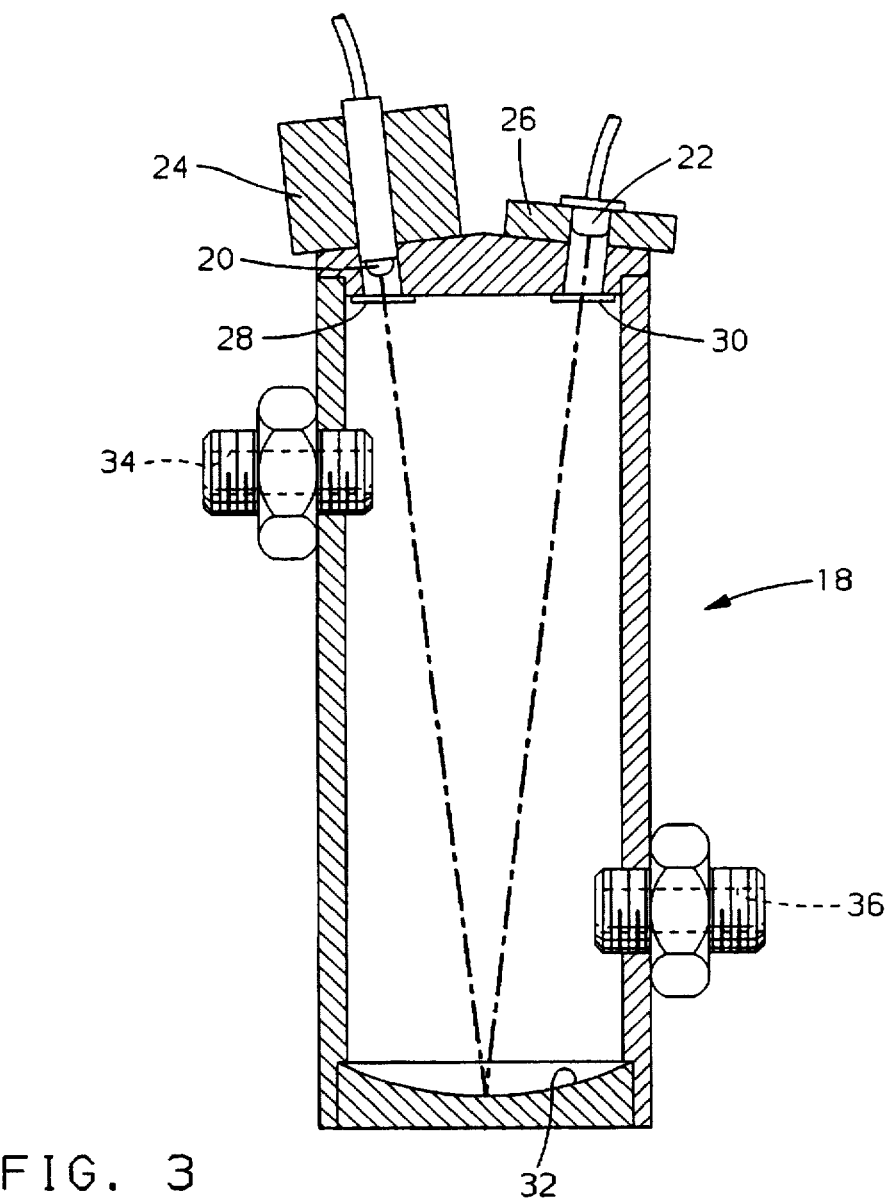
FIG. 3 illustrates an infrared detector used in the present invention.

An infrared detector system as shown in FIG. 3 is operably connected to the sample cell. The infrared detector system includes an light emitting source 20 such as a miniature incandescent lamp. However, only one infrared detector 22, such as a thermopile detector is needed and is positioned on the opposite side of the sample cell from the concave mirror. Aluminum blocks 24, 26 carry the lamp and detector. Microscope cover slides 28, 30 protect the lamp and detector. A concave mirror 32 is placed opposite the ir source. The sample cell includes inlet and outlet ports 34, 36. When measurements are not being made of the exhaust gas with the infrared detector system, the valve is open and the air pump acts as a continuous purge pushing small amounts of clean air through the sample cell into the exhaust. This system prevents contaminants in the automobile combustion exhaust gas such as soot, oil or dirt from contaminating the optics of the infrared detector system.

When a measurement is to be made, the valve is closed so that the exhaust gas flows through the sample cell. During the measurement, the valve cycles such that the environment in the cell alternates between exhaust and clean air on a time scale of a few seconds. This will require a flow of a few tenths of a liter of exhaust gas per minute through the sample cell. Thus, only during the relatively short time periods during which measurements are being made of the exhaust gas would the sample cell and the infrared optics be exposed to the exhaust. Problems from contamination of either the optics in the sample cell or the valve are minimized. By alternate filling the sample cell with exhaust gas and then with air, the requirement that two wavelengths to be examined is removed. This is because measuring the transmitted intensity when the sample cell is purged is equivalent to measurement at the "reference" wavelength. The result is that a simpler, less expensive one-element detector can be used. Because the single-element detector is used, the alignment requirement disappears. Any long term in changes in alignment changes the signal but the ratio of the signals during the reference and hydrocarbon portions of the cycle is unaffected.

An alternative to infrared absorption to detect exhaust hydrocarbons is infrared emission. With this approach, a detector monitors emissions by gas phase hydrocarbons, taking advantage of the fact that emission intensity is proportional to the hydrocarbon concentration. There are several advantages to this technique. First, if only gas phase hydrocarbons are monitored, then contamination of some of the optical surfaces becomes less important. Second, long path lengths which are required for sensitive absorption measurements are unnecessary, so adequate sensitivity can be obtained with much smaller sample cells. Third, sensitivity is in principle higher because emission is an absolute measurement while absorption is a differential measurement. Therefore, in the absence of interfering emission from other sources one is not taking a small difference between large numbers.

Unfortunately, there will certainly be interfering black or grey body emissions from all surfaces which are viewed by the detector. Emission from a black or grey body depends on both its emissivity and its temperature. The exhaust gas is much hotter than the walls, but its emissivity is much lower. The contribution of exhaust emission to the total infrared single from the walls and from gas phase hydrocarbons must be comparable. This problem would be solved if we could modulate the infrared signal from just the gas phase hydrocarbons. To accomplish this the composition in the sample cell is altered from between hot exhaust gas to cool, clean air from the air pump. Assuming that the cell wall temperature can be held constant during these cycles, then the signal during the air part of the cycle can be subtracted from the signal during the exhaust part of the cycle to give the emission from the gas phase hydrocarbons alone. The effect of venting the cell on wall temperature can also be eliminated by measuring the variation of wall temperature or by thermostating the walls. It may be necessary to thermostat the sample cell if it is found that venting it cools it significantly.

The embodiments of the invention in which an exclusive property or privilege is claimed is defined as follows:

1. An on-board diagnostic system comprising:

a combustion engine, and a combustion emission collection system operatively connected to said engine, and an exhaust measuring system constructed and arranged to be useable as the combustion engine is in operation on a regular continuous basis, said exhaust measuring system comprising an exhaust sampling port, a sample cell, and an infrared system;

said exhaust sampling port communicating with the exhaust collection system;

said sample cell communicating with the exhaust sampling port, and an air pump communicating with the sample cell; and said infrared system, having a filter selective for detecting light associated with the presence of hydrocarbon, connected to the sample cell, and wherein said pump is controlled to periodically purge the sample cell of exhaust gas and fill the sample cell with air and wherein the infrared system is controlled to take a first measurement when the sample cell is filled with air and a second measurement, independent of the first measurement, when the sample cell is filled with exhaust gas, and further comprising a comparator for determining the ratio between the first and second measurements, and wherein said infrared system includes only one infrared detector.

2. An on-board diagnostic system as set forth in claim 1 wherein said infrared system is constructed and arranged to measure concentration of pollutants by infrared absorption.

3. An on-board diagnostic system as set forth in claim 1 wherein said infrared system is constructed and arranged to monitor contaminants in the exhaust gas by infrared emissions.

* * * * *